United States Patent
Meier et al.

(10) Patent No.: US 9,643,153 B2
(45) Date of Patent: May 9, 2017

(54) MEMBRANE-SUPPORTED CATALYST REMOVAL IN THE EPOXIDATION OF CYCLIC UNSATURATED C12 COMPOUNDS, FOR EXAMPLE CYCLODODECENE (CDEN)

(71) Applicants: Ralf Meier, Dortmund (DE); Kévin Micoine, Herten (DE); Peter Kreis, Dortmund (DE); Frederik Gluth, Düsseldorf (DE); Markus Priske, Mobile, AL (US)

(72) Inventors: Ralf Meier, Dortmund (DE); Kévin Micoine, Herten (DE); Peter Kreis, Dortmund (DE); Frederik Gluth, Düsseldorf (DE); Markus Priske, Mobile, AL (US)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/714,985

(22) Filed: May 18, 2015

(65) Prior Publication Data

US 2015/0328619 A1    Nov. 19, 2015

(30) Foreign Application Priority Data

May 19, 2014 (DE) .................. 10 2014 209 421

(51) Int. Cl.
| | |
|---|---|
| C07D 301/32 | (2006.01) |
| B01J 19/24 | (2006.01) |
| C07D 225/02 | (2006.01) |
| B01D 61/02 | (2006.01) |
| B01J 31/40 | (2006.01) |
| C07D 301/12 | (2006.01) |

(52) U.S. Cl.
CPC ........ *B01J 19/2475* (2013.01); *B01D 61/027* (2013.01); *B01J 31/4061* (2013.01); *C07D 225/02* (2013.01); *C07D 301/12* (2013.01); *C07D 301/32* (2013.01); *B01D 2311/02* (2013.01); *B01J 2219/24* (2013.01); *B01J 2231/72* (2013.01); *B01J 2531/56* (2013.01); *B01J 2531/64* (2013.01); *B01J 2531/66* (2013.01); *B01J 2531/985* (2013.01); *B01J 2540/42* (2013.01); *Y02P 20/584* (2015.11)

(58) Field of Classification Search
CPC .............. B01D 2311/02; B01D 61/027; B01J 19/2475; B01J 2231/72; B01J 31/4061; C07D 301/32
See application file for complete search history.

(56) References Cited

U.S. PATENT DOCUMENTS

| | | |
|---|---|---|
| 6,610,864 B2 | 8/2003 | Krebs et al. |
| 6,828,449 B2 * | 12/2004 | Herwig ................ C07D 301/12 549/518 |
| 6,861,540 B2 | 3/2005 | Herwig et al. |
| 7,253,329 B2 | 8/2007 | Herwig et al. |
| 7,601,263 B2 * | 10/2009 | Ebert .................... B01D 61/027 210/490 |
| 8,969,628 B2 | 3/2015 | Priske et al. |
| 2004/0099603 A1 * | 5/2004 | Livingston ........... B01D 61/025 210/649 |
| 2012/0046503 A1 | 2/2012 | Priske et al. |
| 2012/0279922 A1 * | 11/2012 | Haensel ............... B01D 67/009 210/650 |
| 2014/0296549 A1 * | 10/2014 | Boam ..................... A23D 9/04 554/191 |
| 2014/0343327 A1 | 11/2014 | Hamers et al. |
| 2016/0082393 A1 | 3/2016 | Priske et al. |
| 2016/0158703 A1 | 6/2016 | Priske et al. |

FOREIGN PATENT DOCUMENTS

| | | |
|---|---|---|
| CA | 1 175 055 A | 9/1984 |
| CA | 2 199 810 A1 | 3/1996 |
| CA | 2199810 A1 | 3/1996 |
| DE | 30 27 349 A1 | 2/1981 |
| EP | 0 781 116 A1 | 7/1997 |
| EP | 1 205 474 B1 | 7/2004 |
| EP | 1 411 051 B1 | 6/2006 |
| EP | 1 411 050 B1 | 3/2007 |
| WO | WO 96/08213 | 3/1996 |
| WO | WO 96/08213 A1 | 3/1996 |
| WO | WO 00/44704 A1 | 8/2000 |
| WO | WO2010/097376 A1 | 9/2010 |
| WO | WO 2011/067054 A1 | 6/2011 |
| WO | WO2013/034690 A1 | 3/2013 |
| WO | WO2014/083952 A1 | 11/2014 |
| WO | WO2014/183952 A1 | 11/2014 |
| WO | WO2015/014741 A1 | 2/2015 |

OTHER PUBLICATIONS

Timofeera et al. (Russian Chemical Bulletin, International Edition, vol. 52, No. 2, pp. 480-486—provided by applicants).*
Haensel (US 2012/0279922) and Nair (Desalination 147 (2002) 301-306).*
Chowdhury (Chem. Eur. J. 2006, 12, 3061-3066).*
Sankhanilay Roy Chowdhury, et al., "Recovery of Homogeneous Polyoxometallate Catalysts from Aqueous and Organic Media by a Mesoporous Ceramic Membrane without Loss of Catalytic Activity", Chemistry A European Journal, vol. 12, No. 11, (2006), pp. 3061-3066.
Wolfgang A. Herrmann, et al., "Methyltrioxorhenium as catalyst for olefin oxidation", Angewandte Chemie International Edition , (Dec. 1991), 10 pages.
M. N. Timofeeva, et al. "Epoxidation of cycloolefins with hydrogen peroxide in the presence of heteropoly acids combined with phase transfer catalyst" Russian Chemical Bulletin, International Edition, vol. 52, No. 2, Feb. 2003, pp. 480-486.

(Continued)

*Primary Examiner* — Valerie Rodriguez-Garcia
(74) *Attorney, Agent, or Firm* — Oblon, McClelland, Maier & Neustadt, L.L.P.

(57) ABSTRACT

A homogeneous catalyst system is removed from a reaction mixture of two liquid phases by separating the two liquid phases with a membrane having at least one separation-active layer in such a way that the homogeneous catalyst system is at least partially concentrated in a membrane retentate; wherein the reaction mixture contains at least one partially epoxidized cyclic unsaturated compound having twelve carbon atoms; and wherein the membrane separation-active layer contains crosslinked a silicone acrylate and/or polydimethylsiloxane and/or polyimide.

13 Claims, 1 Drawing Sheet

(56) References Cited

OTHER PUBLICATIONS

T.C.O. Mac Leod, et al. "An environmentally friendly triphasic catalytic system: Mn(salen) occluded in membranes based on PDMS/PVA" Applied Catalysis B: Environmental, vol. 100, No. 1-2, 2010, pp. 55-61.
U.S. Appl. No. 14/714,985, filed May 18, 2015, Meier, et al.
U.S. Appl. No. 14/814,984, filed Jul. 31, 2015, Micoine, et al.

Sankhanilay Roy Chowdhury, et al., "Recovery of Homogeneous Polyoxornetaliate Catalysts from Aqueous and Organic Media by a Mesoporous Ceramic Membrane without Loss of Catalytic Activity", Chemistry A European Journal, Vol. 12, No. 11, (2006), pp. 3061-3066.
Wolfgang a. Herrmann, e al., "Methyltrioxorhenium as catalyst for olefin oxidation", Angewandte Chernie International Edition, (Dec. 1991), 10 pages.

* cited by examiner

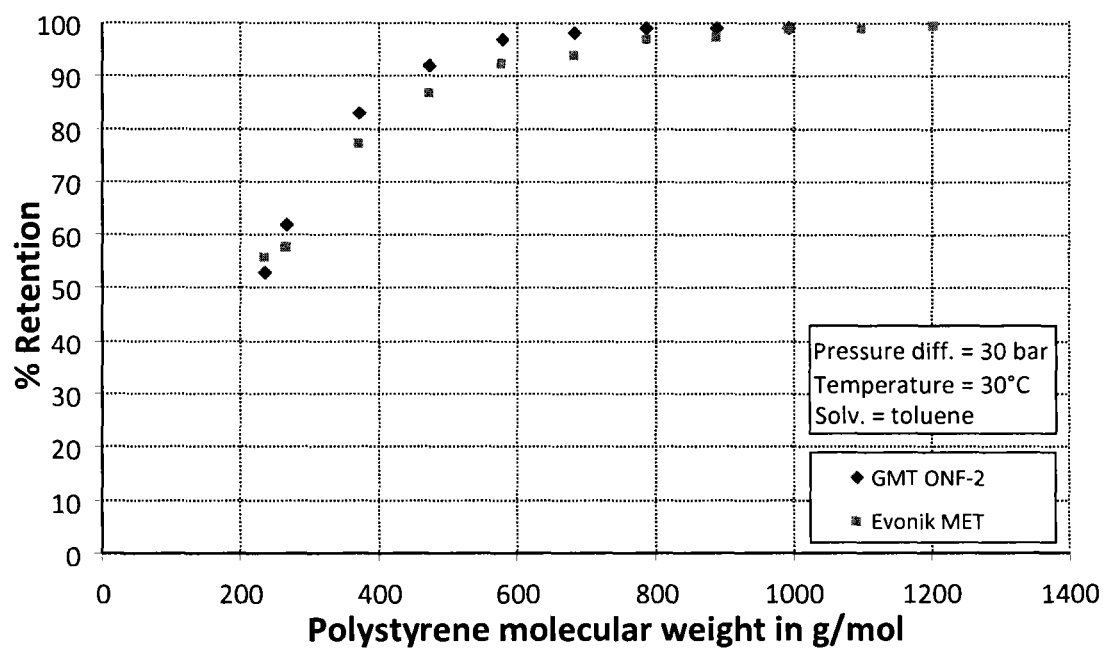

MEMBRANE-SUPPORTED CATALYST REMOVAL IN THE EPOXIDATION OF CYCLIC UNSATURATED C12 COMPOUNDS, FOR EXAMPLE CYCLODODECENE (CDEN)

BACKGROUND OF THE INVENTION

Field of the Invention

The present invention relates to a method of removing homogeneous catalysts from organic reaction mixtures.

Discussion of the Background

Methods of recovering catalysts from reaction mixtures are of fundamental importance for the economics of industrial chemical processes since without these methods it would be impossible to reuse often costly catalyst material. Yet, the recovery of catalysts presents those skilled in the art with particular challenges, particularly when homogeneous catalysis is concerned. Since in homogeneous catalysis the catalyst and the reactants are in the same phase it is usually impossible to separate the catalyst from the reactants by simple physical separation methods, for example centrifugation or conventional filtration.

One way to recover homogeneous catalysts is using nanofiltration. Nanofiltration is a pressure-driven membrane method wherein a specific membrane is used to remove selected dissolved components from a liquid phase. The selectivity of the membrane may be based on various mechanisms. In the size exclusion mechanism, the retained dissolved components are prevented from permeating the membrane by steric effects. Removal thus depends on the size of the dissolved component and the mean pore size of the membrane. Here, the membrane is usually characterized by the molecular weight of the retained components. In an electrostatic mechanism, the selectivity of the membrane arises from the surface charge on the membrane and the charge on the dissolved components. A charge of the same sign causes electrostatic repulsion and thus retention of the dissolved components. It is thus also possible, for example, to employ nanofiltration to remove heavy metal ions from aqueous solutions. Finally, separation may also be based on the membrane forming a separate phase which dissolves the constituents of the mixture to be separated. Separation is then due to the different solubilities and diffusion rates of the components. The resulting transport rates of individual components may vary to such an extent that said components are depleted in one another, i.e., separated. The separation effects utilized in a membrane are thus distinctly more complex than the purely mechanical screening effect utilized in filters.

Membrane separation is employed in water and wastewater treatment for example. One problem with using nanofiltration in other environments is often the poor stability of the membrane in solutions other than aqueous solutions. The stability of the membrane towards organic solvents in particular is often insufficient. The membrane moreover utilizes a wide variety of interactions with the medium to be separated to perform its separation duty. Choosing a membrane material suitable for a particular separation duty is therefore anything but trivial.

Chowdhury et al. employ a ceramic membrane to recover homogeneous catalysts from organic solvents in the epoxidation of olefins:

S. R. Chowdhury et al., "Recovery of homogeneous polyoxometallate catalysts from aqueous and organic media by a mesoporous ceramic membrane without loss of catalytic activity", Chemistry—A European Journal, 2006, Vol. 12, Issue 11, pp. 3061-3066

A membrane particularly suitable for use in the presence of epoxidized cyclic unsaturated $C_{12}$ compounds with hydrogen peroxide has not hitherto been identified.

SUMMARY OF THE INVENTION

The present invention relates to a method of removing homogeneous catalyst systems from organic reaction mixtures. It is an object of the present invention to specify a method employed in reaction mixtures for the epoxidation of cyclic unsaturated $C_{12}$ compounds. This object and other objects are achieved by employing a membrane whose separation-active layer comprises crosslinked silicone acrylates and/or polydimethylsiloxane (PDMS) and/or polyimide.

In one embodiment, the present invention relates to a method of removing a homogeneous catalyst system from a reaction mixture which comprises two liquid phases, said method comprising:

separating the two liquid phases of said reaction mixture with a membrane comprising at least one separation-active layer in such a way that the homogeneous catalyst system is at least partially concentrated in a membrane retentate;

wherein the reaction mixture comprises at least one partially epoxidized cyclic unsaturated compound comprising twelve carbon atoms; and wherein the membrane separation-active layer comprises crosslinked a silicone acrylate and/or polydimethylsiloxane and/or polyimide.

In another embodiment, the present invention relates to an apparatus for the epoxidation of a cyclic unsaturated $C_{12}$ compound with hydrogen peroxide, said apparatus comprising:

a reactor for carrying out the reaction, wherein the walls of the reactor are at least partially furnished with a separation-active layer of crosslinked silicone acrylates and/or polydimethylsiloxane.

In yet another embodiment, the present invention relates to the above apparatus which is suitable for carrying out simultaneously an epoxidation of a cyclic unsaturated $C_{12}$ compound with hydrogen peroxide and a method of removing a homogeneous catalyst system from a reaction mixture as described above.

In another embodiment, the present invention relates to a method of synthesizing lactams using the epoxidized cyclic unsaturated compound comprising twelve carbon atoms obtained from the method of removing a homogeneous catalyst system from a reaction mixture as described above.

BRIEF DESCRIPTION OF DRAWINGS

The FIGURE is a graph showing the separation limit of a membrane.

DETAILED DESCRIPTION OF THE INVENTION

It is an object of the present invention to specify a membrane material for removing homogeneous catalyst systems that is employable in reaction mixtures for the epoxidation of cyclic unsaturated $C_{12}$ compounds with hydrogen peroxide.

Methods of epoxidation of cyclic $C_{12}$ compounds using homogeneous catalysts are disclosed in Angew. Chem. (1991), 103, 1706-1709, EP1205474, EP1411050 and EP1411051 for example.

A particular focus of the present invention is the removal of homogeneous transition metal catalyst systems dissolved in the organic phase using a phase transfer reagent. Phase transfer reagents employed here are in particular tertiary and quaternary ammonium compounds. A nanofiltration method specifically adapted for this catalyst system has not hitherto been disclosed.

Extensive research has revealed that membranes comprising a separation-active layer of cross-linked silicone acrylates and/or polydimethylsiloxane and/or polyimide are useful for removing such a catalyst system from the reaction mixture of an epoxidation of cyclic unsaturated $C_{12}$ compounds. The separation-active layer may comprise each of these three membrane materials individually or in combination.

The invention thus provides a method of removing a homogeneous catalyst system from a reaction mixture wherein a membrane comprising at least one separation-active layer separates the reaction mixture in such a way that the homogeneous catalyst system is concentrated in the membrane retentate at least to an extent wherein the reaction mixture comprises at least one partially epoxidized cyclic unsaturated compound comprising twelve carbon atoms and the membrane separation-active layer comprises crosslinked silicone acrylates and/or polydimethylsiloxane (PDMS) and/or polyimide.

The reaction mixture comprises two immiscible or poorly miscible liquid phases. One of the phases comprises substantially water (aqueous phase). This phase may additionally comprise hydrogen peroxide, catalyst, phase transfer reagent and traces of the cyclic unsaturated $C_{12}$ compound, traces of the epoxidized cyclic unsaturated $C_{12}$ compound and traces of the descendent product thereof such as diols for example. The other phase (organic phase) typically comprises substantially epoxidized cyclic unsaturated $C_{12}$ compounds as epoxidation reaction product. Said phase may additionally comprise the reaction mixture comprising the unmodified cyclic unsaturated $C_{12}$ reactant compounds, the catalyst and the phase transfer reagent.

The two liquid phases are separated before the reaction mixture is supplied to the membrane. Said separation may be carried out using a phase separation vessel for example. As such, the reaction mixture is applied to the membrane as a monophasic mixture rather than a biphasic mixture. It is preferable to subject the non-aqueous (organic) phase to membrane separation. The catalyst may also be removed from the aqueous phase using membrane technology. The aqueous and organic phases are thus freed of catalyst separately using one membrane per phase. The membrane used for the aqueous phase may be different from the membrane used for the organic phase. The membrane used for the aqueous phase preferably comprises a membrane material selected from the following: polyamides, aromatic polyamides, polysulphones, polyethersulphones, hydrophobicized polyethersulphones, sulphonated polyethersulphones, cellulose acetate, polypiperazine and polyvinylidene fluoride. By contrast, the organic phase should be separated using a membrane based on silicone acrylate and/or polydimethylsiloxane (PDMS) and/or polyimide.

If reaction mixture phase separation were not to take place, a person skilled in the art is familiar with measures for achieving phase separation such as increasing the polarity of the aqueous phase or changing the density of one phase.

In the context of the present invention, the term cyclic unsaturated $C_{12}$ compounds thus encompasses both the cyclic unsaturated $C_{12}$ compounds used as reactant and the epoxidized cyclic unsaturated $C_{12}$ compounds obtained as product. If the reactant has exactly one multiple bond, the product is a saturated compound on account of the epoxidation of the multiple bond. The membranes employable in accordance with the invention need not consist exclusively of the abovementioned separation-active materials and may also comprise further materials. In particular, the membranes may comprise support or carrier materials to which the separation-active layers have been applied. Such membranes are referred to as laminated or composite membranes. Such laminated membranes thus comprise a support material in addition to the actual separation-active material. Appropriate support materials are disclosed in EP 0 781 116 A1 for example.

Commercially available membranes employable in the method according to the invention include the MPF and SELRO products from Koch Membrane Systems, Inc., the products from Solsep B. V., the STARMEM products from Grace/UOP, the PURAMEM and DURAMEM products from Evonik Industries AG, the NANO-PRO products from AMS Technologies Ltd. and the oNF-1, oNF-2 and NC-1 membranes from GMT Membrantechnik GmbH.

The method according to the invention recovers homogeneous catalysts for the epoxidation of cyclic unsaturated C12 compounds directly from the reaction mixture following successful epoxidation. This ensures a particularly economical reaction regime since the recovered catalyst may be reused for further epoxidation reactions.

The cyclic unsaturated compound comprising twelve carbon atoms is preferably cyclododecene (CDEN). CDEN is prepared, for example, by selective hydrogenation of cyclododecatriene which is in turn obtainable by trimerization of butadiene. The epoxidation gives monoepoxycyclododecane.

The method according to the invention removes related art homogeneous epoxidation catalyst systems. These are typically transition metal catalysts, in particular catalysts comprising tungsten, molybdenum or vanadium, as described in WO 00/44704 (A1) and DE 30 27 349 A1 for example.

The catalyst system typically comprises a derivative of tungsten, molybdenum and/or vanadium. Useful derivatives include in particular an oxide, a mixed oxide, an oxoacid, a salt of an oxoacid, a carbonyl derivative, a sulphide, a chloride, an oxychloride or a stearate of the elements tungsten, molybdenum and/or vanadium.

Useful derivatives include, for example, the metal carbonyls $W(CO)_6$ and $Mo(CO)_6$, the oxides $MoO_2$, $MoO_5$, $Mo_2O_3$, $MoO_3$, $WO_2$, $W_2O_5$, $WO_3$, $VO_2$, $V_2O_3$ and $V_2O_5$ and the sulphides $WS_2$ and $WS_3$. Further examples include the oxoacids $H_2WO_4$ and $H_2MoO_4$, more specifically the alkali metal and alkaline earth metal salts thereof. Existing epoxidation catalysts comprise, for example, tungstate or molybdate, in particular sodium tungstate $Na_2WO_4$ or sodium molybdate $Na_2MoO_4$.

These compounds are usually converted into the catalytically active compound in situ. This is preferably effected by reaction with a phosphorus and/or arsenic derivative. Compounds particularly suitable therefor are oxides, oxoacids, salts of oxoacids, sulphides, chlorides, oxychlorides or fluorides of phosphorus and/or arsenic.

The catalyst thus preferably comprises a catalytically active compound obtained by reacting a tungsten, molybdenum or vanadium derivative with a phosphorus or arsenic derivative. In one particularly preferred embodiment, the catalytically active transition metal compound is formed in situ by reaction of sodium tungstate with phosphoric acid.

The catalysts described often comprise a phase transfer reagent which makes it possible to transfer the inherently water-soluble catalyst into the organic $C_{12}$ phase.

In one particularly preferred embodiment of the present invention, the catalyst thus comprises a tungsten, molybdenum or vanadium derivative in combination with a phase transfer reagent.

Phase transfer reagents useful here include in particular ternary and quaternary ammonium compounds as described in DE 30 27 349 A1 for example.

In the context of the present invention, the term ternary ammonium compounds is to be understood as meaning organic ammonium compounds where three valences of the nitrogen atom are bound to organic radicals. These include in particular compounds of empirical formula $NR_3$, where each instance of R is an organic radical, imine compounds of formula $R=NR$ as well as N-alkylated heteroaromatics.

One example of a useful phase transfer reagent is the trioctylamine available under the name Alamine. The octyl radicals may have been at least partially replaced by decyl radicals. Said amine is a preferred phase transfer reagent of the present invention.

In the context of the present invention, the term quaternary ammonium compounds is to be understood as meaning organic ammonium compounds where all four valences of the nitrogen atom are bound to organic radicals. These include in particular compounds of empirical formula $NR_4^+ X^-$, where all four instances of R are organic radicals, imine compounds of formula $R=NR_2^+X^-$ as well as N-alkylated heteroaromatics where in each case $X^-$ is the associated anion.

One example of a useful phase transfer reagent is the tricaprylylmethylammonium chloride available under the name Aliquat 336.

The compounds known as esterquats have also proven useful as phase transfer reagents for carrying out epoxidation reactions. In the context of the present invention, the term esterquat is to be understood as meaning quaternary ammonium compounds bearing at least one carboxylic ester group.

In one particularly preferred embodiment, the catalyst system thus comprises as a quaternary ammonium compound an esterquat of formula (I)

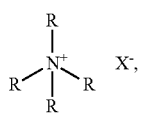
(I)

where the substituents R are independently identical or different alkyl or alcohol groups comprising from 1 to 4 carbon atoms and at least one of the substituents R is an alcohol group which comprises from 1 to 4 carbon atoms and which has been esterified with a saturated or unsaturated fatty acid comprising from 1 to 30 carbon atoms and $X^-$ is a counteranion. The unsaturated fatty acids may be mono- or polyunsaturated. Saturated or unsaturated fatty acids comprising from 8 to 20 carbon atoms are particularly preferable here, those comprising from 16 to 18 carbon atoms being most preferable.

Examples of preferred counteranions $X^-$ include chloride, $Cl^-$, and methylsulphate, $CH_3SO_4^{31}$.

The substituents R in formula (I) are independently identical or different alkyl or alcohol groups comprising from 1 to 4 carbon atoms and at least one of the substituents R is an esterified alcohol group. The alcohol groups are preferably monohydric alcohols. Useful alkyl groups are in particular methyl, ethyl, propyl, isopropyl, n-butyl, isobutyl, sec-butyl and tert-butyl. Useful alcohols include in particular all monohydroxylated derivatives of these alkyl groups, in particular hydroxymethyl, 1-hydroxyethyl, 2-hydroxyethyl, 1-hydroxypropyl, 2-hydroxypropyl, 3-hydroxypropyl, 1-hydroxy-1-methyl(ethyl), 2-hydroxy-1-methyl(ethyl), 1-hydroxybutyl, 2-hydroxybutyl, 3-hydroxybutyl, 4-hydroxybutyl, 1-hydroxy-1-methyl(propyl), 2-hydroxy-1-methyl(propyl), 3-hydroxy-1-methyl(propyl), 1-hydroxymethyl(propyl) and 1-hydroxymethyl-1-methyl(ethyl).

Compounds which have proven particularly suitable are the quaternary ammonium compound esters according to formulae (II) and (III)

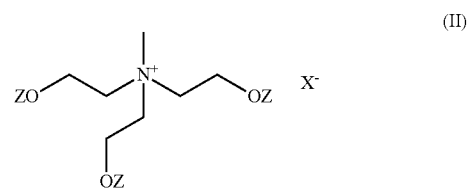

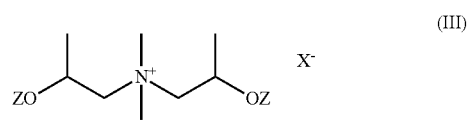

where Z denotes one or more saturated or unsaturated fatty acids comprising from 1 to 30 carbon atoms and $X^-$ is a counteranion. Saturated or unsaturated fatty acids comprising from 8 to 20 carbon atoms are particularly preferable here, those comprising from 16 to 18 carbon atoms being most preferable.

The esterquats described are obtainable by esterification of the corresponding tertiary alcoholamines, for example N-methyldiisopropanolamine or triethanolamine, with a suitable fatty acid and subsequent reaction with a suitable alkylating agent, for example dimethyl sulphate, diethyl sulphate or methyl chloride, to give the quaternary alkanolamine compounds.

The esterquats of formulae (I) to (III) are generally available as mixtures of different esters and both the fatty acid group and the number of esterified fatty acid groups per alkanolamine compound may vary. Esterquats are therefore characterized on the basis of their degree of esterification. This is the mean number of esterified fatty acids per alkanolamine compound. The degree of esterification is preferably in the range of from 1 to 2.0, more preferably from 1.2 to 2.0 and most preferably from 1.5 to 1.95. An esterquat having a desired degree of esterification is synthesized by reacting the alkanolamine compound with an amount of fatty acid corresponding to the degree of esterification. The esterification conversion is checked by reference to the acid number following synthesis. The conversion is sufficiently complete when the acid number is below 5 g of KOH per 1 g of solution.

The catalyst is preferably removed using a composite membrane. A composite membrane comprises a support material and a membrane material applied thereto as a separation-active layer. The support material is thus distinct from the separation-active material. It has transpired that composite membranes comprising a porous support material and a layer prepared by crosslinking silicone acrylates or polydimethylsiloxanes are both extremely stable towards the reaction mixture described and bring about a high yield of recovered catalyst. The composite membranes described are particularly suitable for recovering catalysts comprising a derivative of tungsten, molybdenum or vanadium and also the described esterquats as phase transfer reagent.

It is believed that the effectiveness of the composite membrane is based on the transport of the catalyst through the membrane being hindered to a greater extent than the remaining constituents of the reaction mixture, the cyclic unsaturated $C_{12}$ compounds in particular passing through the membrane more rapidly than the catalyst. The layer based on crosslinked silicone acrylates or polydimethylsiloxanes plays a particular role here and is believed to have a determining influence on the diffusion characteristics, hence its description as the separation-active layer. The support material will play only a secondary role in separation performance although its fundamental involvement in performing the separation duty cannot be ruled out due to the complexity of the processes occurring at a membrane.

Useful composite membranes and methods of preparation thereof are described in DE19507584, EP1741481 and WO 2011/067054 A1 for example.

Particularly suitable membranes are characterized in that the silicone acrylates are compounds of formula IV

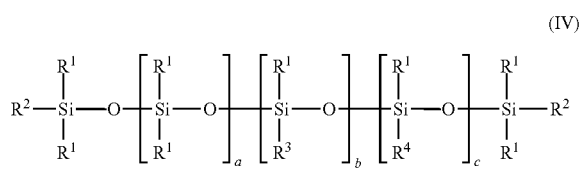

where
a=from 1 to 500, b=from 1 to 25 and c=from 0 to 20,
the substituents $R^1$ are independently identical or different alkyl or aryl groups which comprise from 1 to 30 carbon atoms and which may bear at least one ether, ester, epoxy and/or hydroxy group,
the substituents $R^2$ are independently identical or different substituents selected from the group consisting of $R^1$, $R^3$ and $R^4$,
the substituents $R^3$ are independently identical or different acrylate groups of formulae V or VI

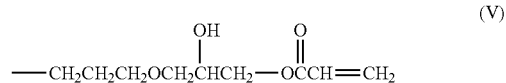

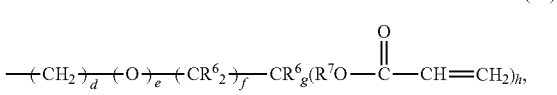

where d=frm 0 to 12, e=from 0 to 1, f=from 0 to 12, g=from 0 to 2, h=from 1 to 3 and g+h=3, the substituents $R^6$ are independently identical or different alkyl or aryl groups comprising from 1 to 30 carbon atoms or hydrogen,
the groups $R^7$ are identical or different divalent hydrocarbon radicals, preferably —$CR^6{}_2$— and in particular $CH_2$,
the substituents $R^4$ are independently identical or different polyether groups of formula (VII)

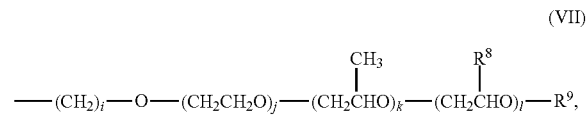

where i=from 0 to 12, j=from 0 to 50, k=from 0 to 50 and l=from 0 to 50,
the substituents $R^8$ are identical or different alkyl or aryl groups comprising from 2 to 30 carbon atoms and
$R^9$ is an alkyl, aryl or acyl group comprising from 2 to 30 carbon atoms or hydrogen.

The various monomers of the building blocks indicated in the formulae (siloxane chains and/or polyoxyalkylene chains) may each have a blockwise construction with any number of blocks in any sequence or form a statistical distribution. The indices indicated in the formulae are to be regarded as statistical mean values.

It is particularly preferable when the separation-active membrane material is constructed in a plurality of layers by crosslinking silicone acrylates of formula IV.

WO 2011/067054A1 discloses such a membrane.

A particularly advantageous family of membranes is obtainable by curing a mixture of different silicone acrylates. The separation limit, degree of crosslinking and hydrophilicity are virtually infinitely variable over hitherto unknown ranges through the choice of mixture.

The separation-active layer itself advantageously comprises one or more layers prepared by curing a mixture of different silicone acrylates. Particularly advantageous mixtures consist of at least the following components:

a) one or more silicone acrylates having a silicon content of more than 29% by weight, preferably one or more silicone acrylates of formula IV having a silicon content of more than 29% by weight and in particular one or more silicone acrylates of formula IV with b=c=0 and having a silicon content of more than 29% by weight, and b) one or more silicone acrylates having a silicon content of less than 27.5% by weight, preferably one or more silicone acrylates of formula IV having a silicon content of less than 27.5% by weight and in particular one or more silicone acrylates of formula IV with c>3 and having a silicon content of less than 27.5% by weight, where for component a) a=from 25 to 500, preferably from 25 to 300 and in particular is 30-200, b=from 0 to 15, preferably from 0 to 8 and in particular is 0, and c=from 0 to 20, preferably from 0 to 10 and in particular is 0, with the proviso that when b=0, $R^2=R^3$; and where for component b) a=from 1 to 24, preferably from 5 to 20, more preferably from 10 to 20 and in particular is 10, 11, 12, 13, 14, 15, 16 or 17, b=from 0 to 25, preferably from 3 to 10 and more preferably is 3, 4, 5, 6, 7 or 8, and c=from 0 to 20, preferably from 0 to 10 and more preferably is 0, 1, 2, 3 or 4, with the proviso that that when b=0, $R^2=R^3$.

The mixtures preferably comprise components a) and b) in a mass ratio of from 10 to 1 to 1 to 10, in particular in a ratio of from 2 to 8 to 8 to 2.

Different silicone acrylates may be characterized by the proportion of silicon they contain. The more organic substituents are bonded to the siloxane scaffold and the longer these substituents the smaller is said proportion of silicon. When the composite membrane is coated using the mixtures of components a) and b) described hereinabove, component a) is preferably a silicone acrylate having a silicon content of >29% by weight and component b) is preferably a silicone acrylate having a silicon content of <27.5% by weight.

The silicone acrylates of formula IV are obtainable by curing with a photoinitiator using electromagnetic radiation of <800 nm in wavelength and/or electron beams. Curing is in particular effected using UV radiation at a wavelength of <400 nm.

Useful carrier membranes are generally solvent-resistant porous three-dimensional structures, for example fibrous nonwoven webs, microfiltration membranes, ultrafiltration membranes or separators, for example battery separators such as Separion® (trade mark of Evonik Degussa GmbH) and Solupor.

Particularly suitable carrier membranes consist of polyacrylonitrile, polyimide, polyether ether ketone, polyvinylidene fluoride, polyamide, polyamide-imide, polyethersulphone, polybenzimidazole, sulphonated polyether ketone, polyethylene, polypropylene or mixtures thereof.

Polyimide carrier membranes and polyacrylonitrile carrier membranes have proven particularly suitable. One of the two materials is thus preferably employed as carrier material within the membrane.

The membrane to be employed in accordance with the invention may be characterized by reference to a separation curve. In the context of the present invention, the separation curve is determined on the basis of the filtration at a temperature of 30° C. and a transmembrane pressure difference of 30 bar in a model system comprising polystyrene oligomers of defined molecular mass dissolved in toluene. Separation curves generated using this model system give an indication as to which membrane to choose. The separation limits observed in the real system generally diverge from those determined in the model system on account of the different interactions of the real system with the membrane compared to the model system.

It is particularly preferable when the membrane to be employed in accordance with the invention exhibits a separation limit profile of more than 97% retention for molecular weights above 1000 g/mol and less than 80% retention for molecular weights below 300 g/mol.

The FIGURE is a graph showing the separation limit of a particularly suitable membrane. Here, the separation limit was determined in established fashion with polystyrene in toluene at a separation temperature of 30° C. and a transmembrane pressure of 30 bar.

The filtration according to the invention of the reaction mixture is generally a pressure-driven process. This means that a pressure difference (transmembrane pressure difference also known as "transmembrane pressure") is applied along the membrane in order to force permeation of the reaction mixture through the membrane. The transmembrane pressure is preferably from 5 to 80 bar, more preferably from 10 to 60 bar and in particular from 30 to 40 bar.

The temperature during the filtration may be adjusted according to the temperature stability of the membrane and the reaction mixture. It is advantageous to choose as high a temperature as possible in order to reduce the viscosity of the reaction mixture and thus expedite the filtration. The filtration is preferably carried out at a temperature of from 25° C. to 160° C., more preferably from 40° C. to 110° C. and in particular from 60° C. to 90° C.

The method according to the invention concentrates the catalyst system in the retentate. The term "retentate" is understood by membrane specialists to mean the effluent from the membrane withdrawn upstream of the membrane. The material which passes through the membrane is known as "permeate" and is withdrawn downstream of the membrane. Here, the amount of catalyst retained may be established based on the amount of retained transition metal. The method according to the invention in particular retains in the retentate more than 50% of the transition metal based on the total amount of transition metal in the reaction mixture prior to filtration. The method preferably retains more than 70% of the transition metal, more preferably more than 90%. When a phase transfer reagent is employed, it will generally achieve a retention different from the transition metal. Said phase transfer reagent is nevertheless concentrated in the retentate. The entire catalyst system is therefore concentrated in the retentate at least to an extent. The transition metal may be detected using ICP-MS (inductively coupled plasma mass spectrometry) or XRF (X-ray fluorescence analysis).

Tungsten and phosphorus are determined using ICP-OES with a spectrometer from Agilent. Since only acidic aqueous solutions may be analysed, the samples must first be digested by microwave digestion (UltraClave from MLS).

Nitrogen determination is effected by oxidative combustion analysis (at 1050° C. in a quartz tube under an oxygen stream) with subsequent chemoluminescence detection of the excited $NO_2$ formed from NO in the presence of ozone.

In one embodiment of the method, the filtration is carried out in a specific separation apparatus comprising the composite membrane according to the invention. Here, the separation apparatus is not part of the reactor in which the epoxidation reaction is carried out. The reaction mixture to be separated may either be withdrawn from the epoxidation reactor in its entirety and supplied to the separation apparatus or a portion of reaction mixture may be continuously withdrawn from the epoxidation reactor and supplied to the separation apparatus. The latter variant is advantageous in particular when the epoxidation reaction is carried out as a continuous process. It is moreover advantageous when the retentate obtained in the filtration is returned to the epoxidation reactor.

In one alternative embodiment, the composite membrane is part of the epoxidation reactor. For example, the walls of the epoxidation reactor may have been at least partially fabricated from the composite membrane or the membrane has been situated directly in the reaction chamber in some other way. Epoxidation and filtration may thus be effected simultaneously and the reaction mixture freed of catalyst and comprising a mixture of reaction product and reactant may therefore be continuously discharged. A corresponding apparatus for the epoxidation of cyclic unsaturated $C_{12}$ compounds with hydrogen peroxide comprising a reactor for carrying out the reaction, said reactor having walls at least partially furnished with a separation-active layer of crosslinked silicone acrylates and/or polydimethylsiloxane (PDMS) and/or polyimide, thus also forms part of the invention subject-matter.

Likewise forming part of the invention subject-matter is the use of such an apparatus for carrying out simultaneously an epoxidation of cyclic unsaturated $C_{12}$ compounds and the corresponding catalyst removal at the membrane integrated into the wall.

The invention further provides a method of synthesizing lactams (lactam method according to the invention) using the epoxidized cyclic unsaturated $C_{12}$ compounds obtained from the abovementioned invention method of removing a homogeneous catalyst system.

The epoxidized cyclic unsaturated $C_{12}$ compounds may subsequently be hydrogenated in the presence of hydrogen and a catalyst comprising a noble metal and a metal oxide. This gives the corresponding ketone and as the case may be the alcohol derivative. If the ketone is obtained as a mixture with the corresponding alcohol derivative, the alcohol may be dehydrogenated to give the ketone. The ketone may subsequently be oximated. The Beckmann rearrangement to give the lactam may be carried out as a subsequent step using sulphuric acid or cyanuric chloride. The lactams may be subjected to further processing by polycondensation to give polyamides.

The hydrogenation, the dehydrogenation, the oximation, the Beckmann rearrangement and the condensation reaction are known to a person skilled in the art.

One preferred embodiment of the lactam method according to the invention comprises preparing laurolactam from monoepoxycyclododecane.

In the context of the preferred lactam method, monoepoxycyclododecane is obtainable by the following reaction steps: 1,3-butadiene is reacted to give cyclododecatriene by cyclotrimerization. This is followed by a hydrogenation to give cyclododecene. The cyclododecane epoxide is obtained by subsequent epoxidation.

Having generally described this invention, a further understanding can be obtained by reference to certain specific examples which are provided herein for purposes of illustration only, and are not intended to be limiting unless otherwise specified.

EXAMPLES

Example 1

In a first step, a catalyst solution was made up. Sodium tungstate salt, concentrated phosphoric acid and water were added thereto. The pH of the solution was adjusted to a strongly acidic value with 10% strength sulphuric acid. In the next step, a stirred tank equipped with a heating jacket was charged with cyclic $C_{12}$ mixture, consisting of 68.5% CDEN and 31.5% cyclododecane (CDAN), the phase transfer reagent aliquat and the catalyst solution described hereinabove. The reactor contents were heated to a temperature of about 80° C. using the heating jacket. A 35% strength solution of $H_2O_2$ in water was then continuously fed into the reactor via a peristaltic pump. Here, the $H_2O_2$ feed rate was adjusted such that the internal temperature of the reactor did not exceed 85° C.

Once the $H_2O_2$ solution had been metered into the reactor the mixture was stirred at a temperature of about 80° C. for several hours, the stirrer was switched off and the phases were then separated. The organic phase was utilized in the membrane filtration experiment which follows.
Membrane Filtration (Organic Phase):

A portion of the organic phase was stirred in a test cell above the test membrane at 23° C. and a transmembrane pressure difference of 39 bar.

The test membrane was a polymer membrane from Evonik MET Ltd. having an active membrane surface area of about 50 cm$^2$.

The membrane separation-active layer consists of silicone acrylate and the carrier layer consists of polyimide.

The permeate flux after an experimental duration of about 2.5 hours was 4.0 kg/(m$^2$h). Determination of samples of retentate and permeate revealed a very high tungsten membrane retention of 99.8% and a nitrogen membrane retention of 95.8%.

Example 2

A portion of the organic phase from example 1 was passed over the test membrane at 55° C. and a transmembrane pressure difference of 30 bar with a cross flow rate of 150 L/h.

The test membrane was a polymer membrane from Evonik MET Ltd. having an active membrane surface area of about 80 cm$^2$. The membrane separation-active layer consists of silicone acrylate and the carrier layer consists of polyimide.

The permeate flux after an experimental duration of about 120 hours was 5.1 kg/(m$^2$h). Determination of samples of retentate and permeate revealed a very high tungsten membrane retention of 99.98% and a nitrogen membrane retention of 87.2%.

Example 3

(Continuous Epoxidation with Downstream Membrane Without Recycling)

In this example, the epoxidation of the cyclic unsaturated $C_{12}$ compounds was carried out as a continuous operation in a 3 stage stirred tank cascade. The stirred tank cascade comprised 2 reactors having a 5 litre nominal capacity and, as a final stage, a stirred tank having a 25 litre nominal capacity. The three reactors comprised a jacket and were heated to a temperature of about 80° C. therewith.

The first reactor of the cascade was supplied with the cyclic unsaturated $C_{12}$ compounds (83.8 Wt % CDEN and 16.2 wt % CDAN), the catalyst components Alamine, sodium tungstate and phosphoric acid and a 50% strength $H_2O_2$ solution. A further quantity of $H_2O_2$ was metered into the second reactor.

The reaction mixture consisting of two liquid phases was passed from the cascade into a phase separation vessel from which the organic phase was supplied to a continuous membrane system using a pump.

Membrane filtration (organic phase with MET membrane, GMT ONF-2, Atech 1 kD) The organic phase was passed over the MET and GMT ONF-2 test membranes at 45° C. and a transmembrane pressure difference of 41.5 bar with a crossflow rate of about 300 L/h. This was done at 600 L/h in the case of the additionally employed ceramic membrane Atech 1 kD.

The experiments of Chowdhury et al. employed commercially unavailable $Al_2O_3$ membranes having pore radii of 2.3 nm and 4.3 nm, i.e., pore diameters of 4.6 nm and 8.6 nm. Example 3 thus employed a commercially available type of ceramic membrane having a particularly low separation limit of 1 kD in order to illustrate the maximum performance of ceramic membranes. It is estimated that this membrane type has a distinctly smaller pore radius than the membranes employed by Chowdhury et al.

The test membranes were a polymer membrane from Evonik MET Ltd. and a membrane of the type ONF-2 from GMT, said membranes having a nominal membrane surface area of 0.6 m$^2$ in the case of the MET membrane and 0.75 m$^2$ in the case of the type ONF-2 membrane. The separation-active layer of the membranes consists of silicone acrylate and the carrier layer consists of polyimide. Atech ceramic membranes having a separation limit of about 1 kD and a membrane surface area of 540 cm$^2$ were also tested.

The tests carried out with the abovementioned setup gave the following process data:

| Membrane | Permeate flux | Membrane retention tungsten | Membrane retention nitrogen |
| --- | --- | --- | --- |
| MET membrane | 2.2 kg/(m²*h) | 99.9% | 73.4% |
| ONF-2 | 2.3 kg/(m²*h) | 99.9% | 74.5% |
| Atech 1 kD | 4.4 kg/(m²*h) | 56.2% | 25.5% |

The low retention values for the Atech 1 kD membrane show that the use of ceramic membranes is not viable for recovery of homogeneous catalysts from organic phases on an industrial scale.

German patent application 102014209421.6 filed May 19, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A method to prepare an epoxidized cyclic unsaturated compound comprising twelve carbon atoms, comprising:
   epoxidizing a cyclic unsaturated compound comprising 12 carbon atoms with hydrogen peroxide in a two phase organic aqueous system in the presence of a homogeneous catalyst and phase transfer reagent;
   separating and removing the aqueous phase to obtain an organic phase containing the epoxidized cyclic unsaturated compound comprising twelve carbon atoms, the homogeneous catalyst and the phase transfer reagent;
   contacting the organic phase with a membrane under a transmembrane pressure of 5 to 80 bar to obtain a permeate comprising the epoxidized cyclic unsaturated compound comprising twelve carbon atoms and a retentate comprising the homogeneous catalyst and phase transfer reagent;
   wherein the membrane is a composite membrane comprising a support material and a membrane separation-active layer comprising a crosslinked silicone acrylate and
   the homogeneous catalyst comprises an oxide, a mixed oxide, an oxoacid, a salt of an oxoacid, a carbonyl derivative, a sulphide, a chloride, an oxychloride or a stearate of an element selected from the group consisting of tungsten, molybdenum and vanadium.

2. The method according to claim 1, wherein the aqueous phase comprises the hydrogen peroxide.

3. The method according to claim 1, wherein the cyclic unsaturated compound comprising twelve carbon atoms is cyclododecene.

4. The method according to claim 3, wherein the phase transfer reagent is a tertiary or quaternary ammonium compound.

5. The method according to claim 4, wherein the phase transfer reagent is a quaternary ammonium compound and is an esterquat of formula (I)

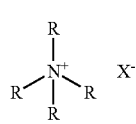

(I)

wherein the substituents R are independently identical or different alkyl or alcohol groups comprising from 1 to 4 carbon atoms and at least one of the substituents R is an alcohol group which comprises from 1 to 4 carbon atoms and which has been esterified with a saturated or unsaturated fatty acid comprising from 1 to 30 carbon atoms and $X^{31}$ is a counteranion.

6. The method according to claim 4, wherein the phase transfer reagent is a quaternary ammonium compound and is a quaternary ammonium compound ester according to formulae (II) and (III)

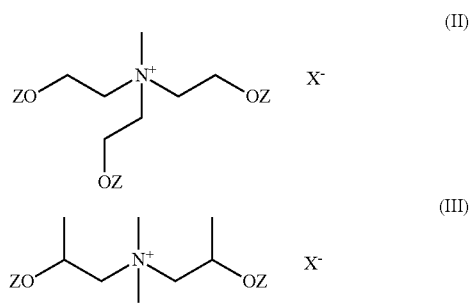

wherein Z denotes one or more saturated or unsaturated fatty acids comprising from 1 to 30 carbon atoms and $X^{31}$ is a counteranion.

7. The method according to claim 1, wherein the silicone acrylate is of formula IV:

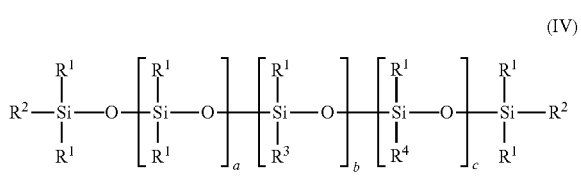

wherein
a is from 1 to 500, b is from 1 to 25 and c is from 0 to 20,
the substituents $R^1$ are independently identical or different alkyl or aryl groups which comprise from 1 to 30 carbon atoms and which may bear at least one ether, ester, epoxy and/or hydroxy group,
the substituents $R^2$ are independently identical or different substituents selected from the group consisting of $R^1$, $R^3$ and $R^4$,
the substituents $R^3$ are independently identical or different acrylate groups of formulae V or VI:

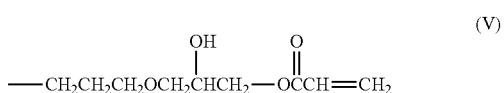

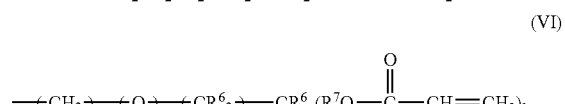

wherein d is from 0 to 12, e is from 0 to 1, f is from 0 to 12, g is from 0 to 2, h is from 1 to 3 and g+h is 3,
the substituents $R^6$ are independently identical or different alkyl or aryl groups comprising from 1 to 30 carbon atoms or hydrogen,
the groups $R^7$ are identical or different divalent hydrocarbon radicals, the substituents $R^4$ are independently identical or different polyether groups of formula (VII):

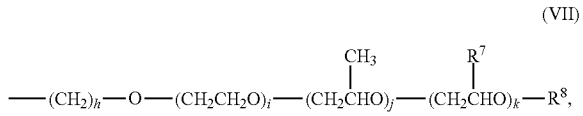

(VII)

wherein i is from 0 to 12, j is from 0 to 50, k is from 0 to 50 and l is from 0 to 50, the substituents $R^8$ are identical or different alkyl or aryl groups comprising from 2 to 30 carbon atoms and $R^9$ is an alkyl, aryl or acyl group comprising from 2 to 30 carbon atoms or hydrogen.

8. The method according to claim 1, wherein the separation-active layer is arranged on a carrier material selected from the group consisting of polyacrylonitrile, polyimide, polyether ether ketone, polyvinylidene fluoride, polyamide, polyamide-imide, polyethersulphone, polybenzimidazole, sulphonated polyether ketone, polyethylene, polypropylene and mixtures thereof.

9. The method according to claim 1, wherein the the applied transmembrane pressure is from 10 to 60 bar.

10. The method according to claim 1, wherein the separation is carried out at a temperature of from 25° C. to 160° C.

11. The method according to claim 7, wherein the groups $R^7$ are identical or different divalent hydrocarbon radicals of the formula $-CR^6{}_2-$.

12. The method according to claim 7, wherein the groups $R^7$ are $CH_2$.

13. The method according to claim 1, wherein the epoxidizing and the separating are carried out simultaneously.

* * * * *

UNITED STATES PATENT AND TRADEMARK OFFICE
CERTIFICATE OF CORRECTION

PATENT NO. : 9,643,153 B2
APPLICATION NO. : 14/714985
DATED : May 9, 2017
INVENTOR(S) : Ralf Meier et al.

Page 1 of 1

It is certified that error appears in the above-identified patent and that said Letters Patent is hereby corrected as shown below:

In the Claims

Column 15, Lines 6-7:

Should read:

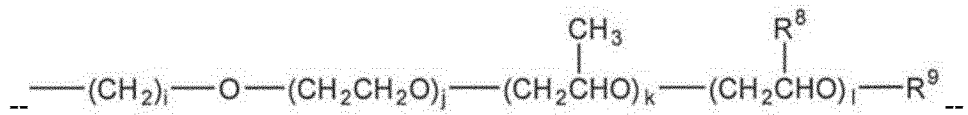

Signed and Sealed this
Sixteenth Day of July, 2019

Andrei Iancu
*Director of the United States Patent and Trademark Office*